(12) United States Patent
Nwulia

(10) Patent No.: US 10,279,006 B2
(45) Date of Patent: May 7, 2019

(54) METHOD, APPARATUS AND KIT FOR THE TREATMENT OF NEURODEGENERATIVE DISEASES AND IMPAIRMENTS

(71) Applicant: Howard University, Washington, DC (US)

(72) Inventor: Evaristus A. Nwulia, Ellicott City, MD (US)

(73) Assignee: Howard University, Washington, DC (US)

( * ) Notice: Subject to any disclaimer, the term of this patent is extended or adjusted under 35 U.S.C. 154(b) by 611 days.

(21) Appl. No.: 14/817,906

(22) Filed: Aug. 4, 2015

(65) Prior Publication Data

US 2015/0335697 A1    Nov. 26, 2015

Related U.S. Application Data

(62) Division of application No. 13/793,592, filed on Mar. 11, 2013, now Pat. No. 9,101,652.

(Continued)

(51) Int. Cl.
| | | |
|---|---|---|
| A61K 36/00 | (2006.01) | |
| A61K 36/752 | (2006.01) | |
| A61K 36/54 | (2006.01) | |
| A61K 36/53 | (2006.01) | |
| A61K 9/00 | (2006.01) | |
| A61M 16/00 | (2006.01) | |
| A61M 16/06 | (2006.01) | |
| A61M 16/12 | (2006.01) | |
| A61M 16/08 | (2006.01) | |
| A61M 16/20 | (2006.01) | |

(Continued)

(52) U.S. Cl.
CPC ............ *A61K 36/752* (2013.01); *A61K 9/007* (2013.01); *A61K 9/0043* (2013.01); *A61K 36/00* (2013.01); *A61K 36/53* (2013.01); *A61K 36/54* (2013.01); *A61M 16/0003* (2014.02); *A61M 16/0057* (2013.01); *A61M 16/0666* (2013.01); *A61M 16/0875* (2013.01); *A61M 16/12* (2013.01); *A61M 16/122* (2014.02); *A61M 16/208* (2013.01); *A61M 16/107* (2014.02); *A61M 21/00* (2013.01); *A61M 2016/003* (2013.01); *A61M 2021/0016* (2013.01); *A61M 2205/8206* (2013.01); *A61M 2205/8237* (2013.01)

(58) Field of Classification Search
CPC ..................................................... A61K 36/00
USPC ....................................................... 424/725
See application file for complete search history.

(56) References Cited

U.S. PATENT DOCUMENTS 5,522,253 A    6/1996 Knight
5,875,783 A    3/1999 Kullik
(Continued)

FOREIGN PATENT DOCUMENTS

WO    2008/103346 A1    8/2008

OTHER PUBLICATIONS

Maxwell, Patrick, and Salnikow, Konstantin, "HIF-1 An Oxygen and Metal Responsive Transcription Factor," Cancer Biology & Therapy, Jan. 2004, vol. 3, No. 1, pp. 29-35.
(Continued)

*Primary Examiner* — Michael V Meller
(74) *Attorney, Agent, or Firm* — Fitch, Even, Tabin & Flannery, LLP

(57) ABSTRACT

A method, apparatus and kit have been discovered which regenerate with the use of odorants the connections of the
(Continued)

Design of the Olfactory Neuroplastic Device neurons of the brain and central nervous system in the treatment of such person afflicted neuro-disorders caused by disease or trauma.

3 Claims, 5 Drawing Sheets

Related U.S. Application Data

(60) Provisional application No. 61/684,316, filed on Aug. 17, 2012.

(51) Int. Cl.
*A61M 21/00* (2006.01)
*A61M 16/10* (2006.01)

(56) References Cited

U.S. PATENT DOCUMENTS

| | | | |
|---|---|---|---|
| 6,145,503 | A | 11/2000 | Smith |
| 6,506,801 | B1 | 1/2003 | Yee et al. |
| 7,013,889 | B2 | 3/2006 | Cronk et al. |
| 7,273,618 | B2 | 9/2007 | Frey, II et al. |
| 7,703,455 | B2 | 4/2010 | Bunke et al. |
| 7,740,014 | B2 | 6/2010 | Djupesland |
| 7,776,312 | B2 | 8/2010 | Frey, II et al. |
| 7,799,337 | B2 | 9/2010 | Levin |
| 8,001,968 | B2 | 8/2011 | Doty et al. |
| 8,192,718 | B1 | 6/2012 | Sung et al. |
| 8,220,457 | B2 | 7/2012 | Berthon-Jones et al. |
| 9,012,490 | B2 | 4/2015 | Nwulia et al. |
| 9,101,652 | B2 | 8/2015 | Nwulia |
| 2004/0014721 | A1 | 1/2004 | Hensley et al. |
| 2005/0090520 | A1 | 4/2005 | Lindquist |
| 2006/0276536 | A1 | 12/2006 | Vander Jagt et al. |
| 2011/0129462 | A1 | 6/2011 | Maggio |
| 2012/0053208 | A1 | 3/2012 | Li et al. |
| 2012/0328701 | A1 | 12/2012 | Edelson et al. |

OTHER PUBLICATIONS

Mesholam, Raquelle I., et al., "Olfaction in Neurodegenerative Disease: A Meta-Analysis of Olfactory Functioning in Alzheimer's and Parkinson's Diseases," Archives of Neurology, Jan. 1998, vol. 55, No. 1, pp. 84-90.
Miwa, Naofumi, and Storm, Daniel R., "Odorant-Induced Activation of Extracellular Signal-Regulated Kinase/Mitogen-Activated Protein Kinase in the Olfactory Bulb Promotes Survival of Newly Formed Granule Cells," The Journal of Neuroscience, Jun. 1, 2005, vol. 25, No. 22, pp. 5404-5412.
Murphy, Claire, et al., "Olfactory Thresholds are Associated with Degree of Dementia in Alzheimer's Disease," Neurobiology of Aging, Jul.-Aug. 1990, vol. 11, No. 4, pp. 465-469.
http://www.neurodegenerationresearch.eu/about/why/, 2014, Why choose Neurodegenerative diseases?
Padhye, S., et al., "Perspectives on Chemopreventive and Therapeutic Potential of Curcumin Analogs in Medicinal Chemistry." Mini Reviews in Medicinal Chemistry, May 2010, vol. 10, No. 5, pp. 372-387.
PCT International Search Report and Written Opinion on Patentablility, International Patent Application PCT/US2014/013158, completed Apr. 11, 2014, 12 pages.
Perry, Elaine, et al., "Medicinal Plants and Dementia Therapy: Herbal Hopes for Brain Aging?" CNS Neuroscience & Therapeutics, 2011, vol. 17, pp. 683-698.
Pfeiffer, Erika, et al., "Studies on the Stability of Turmeric Constituents." Journal of Food Engineering, 2003, vol. 56, pp. 257-259.
Rochefort, Christelle, et al., Enriched Odor Exposure Increases the Number of Newborn Neurons in the Adult Olfactory Bulb and Improves Odor Memory, The Journal of Neuroscience, vol. 22, No. 7, Apr. 1, 2002, pp. 2679-2689.
Ross, T. M., et al., "Intranasal administration of interferon beta bypasses the blood-brain barrier to target the central nervous system and cervical lymph nodes: a non-invasive treatment strategy for multiple sclerosis," Journal of Neuroimmunology, 2004, vol. 151, pp. 66-77.
Ruan, Yang, et al., "Olfactory Dysfunctions in Neurodegenerative Disorders," Journal of Neuroscience Research, Sep. 2012, vol. 90, No. 9, pp. 1693-1700.
Saiyudthong, Somrudee, and Marsden, Charles A., "Acute Effects of Bergamot Oil on Anxiety-Related Behavious and Corticosterone Level in Rats," Phytotherapy Research, 2011, vol. 25, pp. 858-862.
Scharfman, Helen E., and Chao, Moses V., "The Entorhinal Cortex and Neurotrophin Signaling in Alzheimer's Disease and Other Disorders," Cognitive Neuroscience, Sep.-Dec. 2013, vol. 4 Nos. 3-4, pp. 123-135.
Schulz, Carla, et al., Central Nervous and Metabolic Effects of Intranasally Applied Leptin, Endocrinology, vol. 145, No. 6, Jun. 2004, pp. 2696-2701.
Shapiro, Lee A., et al., "Olfactory enrichment enhances the survival of newly born cortical neurons in adult mice," NeuroReport, Jul. 2, 2007, vol. 18, No. 10, pp. 981-985.
Shishodia, Shishir, et al., "Modulation of Transcription Factors by Curcumin," The Molecular Targets and Therapeutic Uses of Curcumin in Health and Disease, Editors: Bharat B. Aggarawal et al., Advances in Experimental Medicine and Biology, 2007, vol. 595, pp. 127-148.
Simmons, Peter A., and Getchell, Thomas V., "Physiological Activity of Newly Differentiated Olfactory Receptor Neurons Correlated With Morphological Recovery From Olfactory Nerve Section in the Salamander," Journal of Neurophysiology, Mar. 1981, vol. 45, No. 3, pp. 529-549.
Snodgrass, Kat, "Alzheimer's protein kills nerve cells in nose, [online]." Retrieved from the Internet on Jul. 11, 2012: <URL: http://www.eurekalert.org/pub_releases/2011-09/sfn-apk092611. php>, Sep. 27, 2011, 1 page.
Sui, Zhihua, et al., "Inhibition of the HIV-1 and HIV-2 Proteases by Curcumin and Curcumin Boron Complexes," Bioorganic & Medicinal Chemistry, 1993, vol. 1, No. 6, pp. 415-422.
Taher, Mohiuddin M., et al., "Curcumin inhibits ultraviolet light induced human immunodeficiency virus gene expression," Molecular and Cellular Biochemistry, 2003, vol. 254, pp. 289-297.
Wang, Ying-Jan, et al., "Stability of Curcumin in Buffer Solutions and Characterization of its Degradation Products," Journal of Pharmaceutical and Biomedical Analysis, 1997, vol. 15, pp. 1867-1876.
Weinberg, Eugene D., and Miklossy, Judith, "Iron Withholding: A Defense Against Disease," Journal of Alzheimer's Disease, 2008, vol. 13, pp. 451-463.
White, Brett, et al., "Does turmeric relieve inflammatory conditions?" The Journal of Family Practice, Mar. 2011, vol. 60, No. 3, pp. 155-166.
Wilson, Robert S., et al., "Odor Identification and Mortality in Old Age," Chemical Senses, Jan. 2011, vol. 36, No. 1, pp. 63-67.
Woo, Cynthia C., et al., "Exposure to a broad range of odorants decreases cell mortality in the olfactory bulb," NeuroReport, May 29, 2006, vol. 17, No. 8, pp. 817-821.
Xu, Ying, et al., "Curcumin reverses impaired hippocampal neurogenesis and increases serotonin receptor 1A mRNA and brain-derived neurotrophic factor expression in chronically stressed rats," Brain Research, 2007, vol. 1162, pp. 9-18.
Yadav, Babasaheb D., "Study of New Curcumin Analogs for the Treatment of ER-alpha Negative Breast Cancers," Doctoral Thesis, The University of Otago, Dunedin, New Zealand, Jan. 4, 2012, 6 pages.
Youngentob, Steven L., et al., "Odorant Threshold Following Methyl Bromide-Induced Lesions of the Olfactory Epithelium," Physiology & Behavior, 1997, vol. 62, No. 6, pp. 1241-1252.
Zhang, Laura, et al., "Curcuminoids enhance amyloid-beta uptake by macrophages of Alzheimer's disease patients," Journal of Alzheimer's Disease, 2006, vol. 10, pp. 1-7.
Letters to the Editors, "Suicidal Ideation Associated With Duloxetine Use: A Case Series," Journal of Clinical Psychopharmacology, Feb. 2008, vol. 28, No. 1, pp. 101-122.

(56) References Cited

OTHER PUBLICATIONS

Du, Zhi-Yun, et al., "Curcumin Analogs as Potent Aldose Reductase Inhibitors," Archiv der Pharmazie Chemistry in Life Science, 2006, vol. 339, pp. 123-128.

Nema, Sandeep, et al., "Excipients and Their Use in Injectable Products," Review Article, PDA Journal of Pharmaceutical Science & Technology, Jul.-Aug. 1997, vol. 51, No. 4, pp. 166-171.

Ribeiro, Sofia, and Horuk, Richard, "The clinical potential of chemokine receptor antagonists," Pharmacology & Therapeutics, 2005, vol. 107, pp. 44-58.

Block, L. H., et al., "Controlled prospective randomised trial on the effects on pulmonary haemodynamics of the ambulatory long term use of nitric oxide and oxygen in patients with severe COPD," Thorax, Apr. 1, 2003, vol. 53, No. 4, pp. 289-293.

Albers, Mark W., et al., "At the Interface of Sensory and Motor Dysfunctions and Alzheimer's Disease," Alzheimer's & Dementia, Jan. 2015, 11(1), pp. 70-98.

Alvarez, Susana, et al., "Human immunodeficiency virus type 1 envelope glycoprotein 120 induces cyclooxygenase-2 expression in neuroblastoma cells through a nuclear factor-κB and activating protein-1 mediated mechanism," Journal of Neurochemistry, 2005, vol. 94, pp. 850-861.

Anand, Preetha, et al., "Bioavailability of Curcumin: Problems and Promises," Molecular Pharmaceutics, Nov. 14, 2007, vol. 4, No. 6, pp. 807-818.

Ataie, Amin, et al., "Curcumin Exerts Neuroprotective Effects Against Homocysteine Intracerebroventricular Injection-Induced Cognitive Impairment and Oxidative Stress in Rat Brain," Journal of Medicinal Food, 2010, vol. 13, No. 4, pp. 821-826.

Atsumi, Toshiko, and Tonosaki, Keiichi, "Smelling lavender and rosemary increases free radical scavenging activity and decreases cortisol level in saliva," Psychiatry Research, vol. 150, 2007, pp. 89-96.

Bagetta, Giacinto, et al., "Neuropharmacology of the essential oil of bergamot," Fitoterapia, vol. 81, 2010, pp. 453-461.

Bai, Xue-Feng, et al., "Nasal administration of myelin basic protein prevents relapsing experimental autoimmune encephalomyelitis in DA rats by activating regulatory cells expressing IL-4 and TGF-β mRNA," Journal of Neuroimmunology, vol. 80, 1997, pp. 65-75.

Barthelemy, S., et al., "Curcumin and curcumin derivatives inhibit Tat-mediated transactivation of type 1 human immunodeficiency virus long terminal repeat," Research in Virology, 1998, vol. 149, pp. 43-52.

Baum, Larry, et al., "Curcumin interaction with copper and iron suggests one possible mechanism of action in Alzheimer's disease animal models," Journal of Alzheimer's Disease, 2004, vol. 6, pp. 367-377.

Benedict, Christian, et al., "Intranasal insulin improves memory in humans," Psychoneuroendocrinology, vol. 29, 2004, pp. 1326-1334.

Born, Jan, et al., "Sniffing neuropeptides: a transnasal approach to the human brain," Nature Neuroscience, vol. 5, No. 6, Jun. 2002, pp. 514-516.

Bovetti, Serena, et al., "Olfactory Enrichment Influences Adult Neurogenesis Modulating GAD67 and Plasticity-Related Molecules Expression in Newborn Cells of the Olfactory Bulb," PLoS ONE, vol. 4, Issue 7, Jul. 2009, 10 pages.

Ceccarelli, Ilaria, et al., "Effects of long-term exposure of lemon essential oil odor on behavioral, hormonal and neuronal parameters in male and female rats," Brain Research, vol. 1001, 2004, pp. 78-86.

Chen, Xue-Qing, et al., "Delivery of Nerve Growth Factor to the Brain via the Olfactory Pathway," Journal of Alzheimer's Disease, vol. 1, 1998, pp. 35-44.

Chiu, Simon S., et al., "Differential Distribution of Intravenous Curcumin Formulations in the Rat Brain," Anticancer Research, 2011, vol. 31, pp. 907-911.

Cole, Greg M., et al., "Neuroprotective Effects of Curcumin," Advances in Experimental Medicine and Biology, 2007, vol. 595, pp. 197-212.

Comford, Eain M., and Comford, Marcia E., "New systems for delivery of drugs to the brain in neurological disease," The Lancet Neurology, vol. 1, Sep. 2002, pp. 306-315.

Conteas, Chris N., et al., "Treatment of HIV-Associated Diarrhea with Curcumin," Digestive Diseases and Sciences, 2009, vol. 54, pp. 2188-2191.

Cos, Paul, et al., "Plant-Derived Leading Compounds for Chemotherapy of Human Immunodefiency Virus (HIV) Infection—An Update (1998-2007)," Planta Medica, 2008, vol. 74, pp. 1323-1337.

Costanzo, Richard M., "Neural Regeneration and Functional Reconnection Following Olfactory Nerve Transection in Hamster," Brain Research, vol. 361, 1985, pp. 258-266.

Devanand, D. P., et al., "Olfactory Deficits in Patients with Mild Cognitive Impairment Predict Alzheimer's Disease at Follow-up," The American Journal of Psychiatry, Sep. 2000, vol. 157, No. 9, pp. 1399-1405.

Doty, Richard L., et al., "Presence of Both Odor Identification and Detection Deficits in Alzheimer's Disease," Brain Research Bulletin, May 1987, vol. 18, No. 5, pp. 597-600.

Du, Zhi-yun, et al., "Alpha-Glucosidase inhibition of natural curcuminoids and curcumin analogs," European Journal of Medicinal Chemistry, 2006, vol. 41, pp. 213-218.

Etchamendy, Nicole, et al., "Alleviation of a Selective Age-Related Relational Memory Deficit in Mice by Pharmacologically Induced Normalization of Brain Retinoid Signaling," The Journal of Neuroscience, Aug. 15, 2001, vol. 21, No. 16, pp. 6423-6429.

Faturi, Claudia Brito, et al., "Anxiolytic-like effect of sweet orange aroma in Wistar rats," Progress in Neuro-Psychopharmacology & Biological Psychiatry, vol. 34, 2010, pp. 605-609.

Fuchs, James R., et al., "Structure-activity relationship studies of curcumin analogues," Bioorganic & Medicinal Chemistry Letters, 2009, vol. 19, pp. 2065-2069.

Gheusi, Gilles, et al., "Importance of newly generated neurons in the adult olfactory bulb for odor discrimination," Proceedings of the National Academy of Sciences, vol. 97, No. 4, Feb. 15, 2000, pp. 1823-1828.

Gilden, Dave, and Smart, Theo, "Curcumin Trial Finds No Activity," GMHC Treatment Issues, Feb. 1996.

Gomez-Pinilla, Fernando, et al., "Natural mood foods: The actions of polyphenols against psychiatric and cognitive disorders," Nutritional Neuroscience, May 2012, vol. 15, No. 3, pp. 127-133.

Gopinath, Bamini, et al., "The Association Between Olfactory Impairment and Total Mortality in Older Adults," The Journals of Gerontology, Series A, Biological Sciences and Medical Sciences, Feb. 2012, vol. 67, No. 2, pp. 204-209.

Gordon, Odaine N., et al., "Vanillin and ferulic acid: not the major degradation products of curcumin," Cell Press, Trends in Molecular Medicine, Jul. 2012, vol. 18, No. 7, pp. 361-363.

Gozes, Illlana, "Neuroprotective peptide drug delivery and development: potential new therapeutics," Trends in Neurosciences, Dec. 2001, vol. 24, No. 12, pp. 700-705.

Graziadei, Pasquale P. C., et al., "Regeneration of olfactory axons and synapse formation in the forebrain after bulbectomy in neonatal mice," Proceedings of the National Academy of Sciences of the United States of America, Oct. 1978, vol. 75, No. 10, pp. 5230-5234.

Graziadei, P. P. C., and Graziadei, G. A. Monti, "Neurogenesis in neuron regeneration in the olfactory system of mammals. I. Morphological aspects of differentiation and structural organization of the olfactory sensory neurons," Journal of Neurocytology, 1979, vol. 8, pp. 1-18.

Gupta, S. P., et al., "Design and Development of Integrase Inhibitors as Anti-HIV Agents," Current Medicinal Chemistry, 2003, vol. 10, pp. 1779-1794.

Harding, Joseph W., et al., "Denervation of the Primary Olfactory Pathway in Mice. V. Long-term Effect of Intranasal ZnSO4 Irrigation on Behavior, Biochemistry and Morphology," Brain Research,1978, vol. 140, pp. 271-285.

Hsu, Chih-Hung, and Cheng, Ann-Lii, "Clinical Studies With Curcumin," Advances in Experimental Medicine and Biology, 2007, vol. 595, pp. 471-480.

(56) References Cited

OTHER PUBLICATIONS

Hurley, Laura L., et al., "Antidepressant-like effects of curcumin in WKY rat model of depression is associated with an increase in hippocampal BDNF," Behavioural Brain Research, 2012, pp. 1-4.

James, John S., "Curcumin: Clinical Trial Finds No Antiviral Effect," The Body, AIDS Treatment News, Mar. 1, 1996, No. 242, 3 pages.

Komiya, Migiwa, et al., "Lemon oil vapor causes an anti-stress effect via modulating the 5-HT and DA activities in mice," Behavioural Brain Research, 2006, vol. 172, pp. 240-249.

Kulkarni, S. K., et al., "Potentials of Curcumin as an Antidepressant," The Scientific World Journal, 2009, vol. 9, pp. 1233-1241.

Kulkarni, S. K., et al., "Evaluation of Antidepressant-Like Activity of Novel Water-Soluble Curcumin Formulations and St. John's Wort in Behavioral Paradigms of Despair," Pharmacology, 2012, vol. 89, pp. 83-90.

Kumar, Anil, et al., "Effect of Curcumin on Intracerebroventricular Colchicine-Induced Cognitive Impairment and Oxidative Stress in Rats," Journal of Medicinal Food, 2007, vol. 10, No. 3, pp. 486-494.

Liao, Kai, et al. "Enriched odor exposure decrease tau phosphorylation in the rat hippocampus and cortex," Neuroscience Letters, 2012, vol. 507, pp. 22-26.

Liu, J.P., et al., "Herbal medicines for treating HIV infection and AIDS (Review)," The Cochrane Library, 2009, Issue 1, 30 pages.

Liu, Yuanbin, et al., "A broadly neuroprotective derivative of curcumin," Journal of Neurochemistry, 2008, vol. 105, pp. 1336-1345.

Mandairon, Nathalie, et al., "Broad activation of the olfactory bulb produces long-lasting changes in odor perception," Proceedings of the National Academy of Sciences of the United States of America, Sep. 5, 2006, vol. 103, No. 36, pp. 13543-13548.

Manna, Sunil K., et al., "Oleandrin Suppresses Activation of Nuclear Transcription Factor-κB, Activator Protein-1, and c-Jun NH2-Terminal Kinase," Cancer Research, Jul. 15, 2000, vol. 60, pp. 3838-3847.

Martončíková, Marcela, et al., "Odor enrichment influences neurogenesis in the rostral migratory stream of young rats," Acta Histochemica, 2011, vol. 113, pp. 326-332.

Masoumi, Ava, et al., "1-alpha,25-dihydroxyvitamin D3 Interacts with Curcuminoids to Stimulate Amyloid-beta Clearance by Macrophages of Alzheimer's Disease Patients," Journal of Alzheimer's Disease, 2009, vol. 17, pp. S1-S4.

METHOD, APPARATUS AND KIT FOR THE TREATMENT OF NEURODEGENERATIVE DISEASES AND IMPAIRMENTS

This application claims the benefit of U.S. Provisional Application Ser. No. 61/684,316, filed Aug. 17, 2012 which is incorporated herein as if fully rewritten.

FIELD

Described herein is a method, apparatus and kit for the treatment of neurodegenerative diseases and impairments with the use of odorants.

BACKGROUND

Alzheimer's disease and dementia are diseases which result in a progressive deterioration of neurons in the brain which causes cognitive deterioration and changes in behavior. With Alzheimer's disease, there is loss of short-term memory and minor forgetfulness which becomes greater as the illness progresses to major memory loss with a relative preservation of older memories. As the disease progresses even further, there is cognitive or intellectual impairment which extends to language degeneration (having difficulty remembering words to being completely unable to speak, read, or write), loss of the ability to execute or carry out learned purposeful movements, and a loss of ability to recognize objects, persons, sounds, shapes, or smells.

Neurons are cells which transmit information via synapses. Neurons connect to each other to form neural networks. Neurons are electrically excitable cells which transmit information by electrical and chemical signaling by synapses which establish connections with other neuron cells. With the progression of Alzheimer's disease and other neurodegenerative diseases, the connectivity of the neurons are adversely affected, such as by the generation of plaque and abnormal proteins called tau proteins.

SUMMARY

The olfactory system beginning in the nose and ending in the cortex and central structures of the brain is the only part of the adult mammalian brain capable of stimulation and regeneration. A method, apparatus and kit have been discovered which regenerate the connections of the neurons of the brain and central nervous systems such that connectivity of the neurons is improved to effect improvement in memory loss, language degeneration, loss of the ability to execute or carry out learned purposeful movements, and a loss of ability to recognize objects, persons, sounds, shapes, or smells. The method includes the delivery of a blend of olfactory enrichment odorants to and through the nose with the delivery of the odorants being under a positive pressure to affect air flow with the odorant at a room temperature (25 degrees C.) delivery rate of air containing odorant of from about 0.5 to about 2 liters per minute. Stimulation of the olfactory neurons in the nose by the odorant blend stimulate neurogeneis (new brain development) in the olfactory brain regions affected neuro-impairments caused by disease or trauma including a cognitive impairment which is a prodromal state in the development of dementia, traumatic brain injury affecting the olfactory regions of the brain, including the frontal lobe, post stroke brain damage involving the frontal lobe regions and olfactory cortices of the brain, Parkinson's disease, schizophrenia and chronic depression. The stimulation of neurogeneis effects a reversal of brain impairments caused by the latter diseases and injuries. In a very important aspect, stimulation of the olfactory neurons in the nose by the odorant blend stimulate neurogeneis in the olfactory brain regions affected by Alzheimer's and other types of dementia and reverse neuropathologies of Alzheimer's disease and dementia, namely hyperphoshorylation of neurofibrillary tangles and tau proteins. The blend of odorants includes a blend of a plurality of odors including citrus (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise at a positive pressure to affect air flow with the odorant delivery rate of from about 0.5 to about 2 liters per minute. In an important aspect, at least three of the odors should be used. And in a very important aspect, the odorants include a blend of citrus (orange), lemon, rosemary and cinnamon at a positive pressure to affect air flow with the odorant delivery rate of from about 0.5 to about 2 liters per minute. The odorants are dispersed in a media which permits them to be swept into the nose for intranasal application of the odorants. In an important aspect, the media is a pharmaceutically acceptable oil, such as mineral oil.

The odorants are in a concentration for each odorant in the range of from about 1 to about 6 weight percent and are driven through the nose to contact olfactory tissue and olfactory receptor neurons. The method brings odorants in contact to this tissue in constant flow or pressure, which is needed to stimulate regeneration (or birth) of olfactory sensory system, which in turn, stimulates the olfactory bulb and olfactory cortices to be active by the intranasal administration of a blend of odorants dispersed in a media, the odorant blend including at least two, preferably three, of the odorants citrus (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise by pumping the blend as part of a flow of gas which includes oxygen and odorant blend. The flow created by a pump creates a positive pressure to create a flow of oxygen and odorant blend through the nose. The concentration of the blend, the ratio of odorants, the rate of flow of the blend and oxygen, a time of treatment, and the ratios of odorants in the blend effective for effecting an improved neuro-function of a person afflicted with the neurodegenerative disease or trauma. In an important aspect for a subject afflicted with a neurodegenerative disease such as Alzheimer's disease and/or dementia, the concentration of the odorant blend, the ratio of odorants, the rate of flow of the blend and oxygen, a time of treatment, and the ratios of odorants in the blend effective for effecting an improvement of at least 50%, preferably 100% and even more preferably 150% in short-term verbal memory of a person afflicted with the neurodegenerative disease, the improvement being measured by a California Verbal Learning Test, Adult, Version 2. The time of treatment is from about 12 hours daily for at least about two weeks, and preferably, for at least about one month. The method contemplates a treatment with a concentration of odorants at positive pressures for a time which effects new brain development (i.e. neuroplasticity) and reversal of pathological features of Alzheimer's disease or dementia in mammals.

The apparatus used to deliver the odorants includes a pump, an air filter, a flow meter, a check valve, an odorant chamber and a cannula configured to deliver the odorant to users afflicted with the neuro degeneration disease. The odorant chamber contains the blend of odorants which are pleasant, tolerable and effect enrichment to human memory after or during the deleterious effects of Alzheimer's disease and dementia and other neurodegenerative diseases. The pump generates a current of filtered air directed into the odorant chamber through a tube with flow-directed valves. This flow is channeled through a user-controlled flow meter, on the outside of the device, for regulation of the rate of flow of odorant containing air/oxygen to the nose. The cannula directing the flow to the nose comes in different shapes and sizes, depending on the shape of a user's nose. The inside of human nose is enriched as the odorants exit the cannula and contact olfactory tissue.

In another aspect, a kit is provided where the kit which includes an apparatus which is configured for the administration of a blend of odorants. The apparatus in the kit comprises a pump; a line which is effective for supplying air to a vessel configured to contain a blend of odorants; a line from the vessel to a cannula configured for lodgment into the nose, the pump being configured to provide a positive pressure and a flow of gas into the cannula and nose at a rate of from about 0.5 to about 2 liters per minute; and at least one additional vessel which includes a second vessel containing a blend of odorants; and wherein the odorant blend in the second vessel includes citrus, lemon, rosemary and cinnamon. The kit is configured for administering the blend including pumping the blend as a part of a flow of gas which includes oxygen and odorant blend. The flow created by the pump creates a positive pressure to create a flow of oxygen and odorant blend through the nose. The concentration of the blend, the ratio of odorants, the rate of flow of the blend and oxygen, a time of treatment, and the ratios of odorants in the blend are effective for effecting an improvement of at least 50%, preferably 100% and even more preferably 150% in short-term verbal memory of a person afflicted with the neurodegenerative disease, the improvement being measured by a California Verbal Learning Test, Adult, Version 2. The kit also may include instructions as to the time of administration of the blend, such as 12 hours daily for one month.

FIGURES

DETAILED DESCRIPTION

Figure 1:
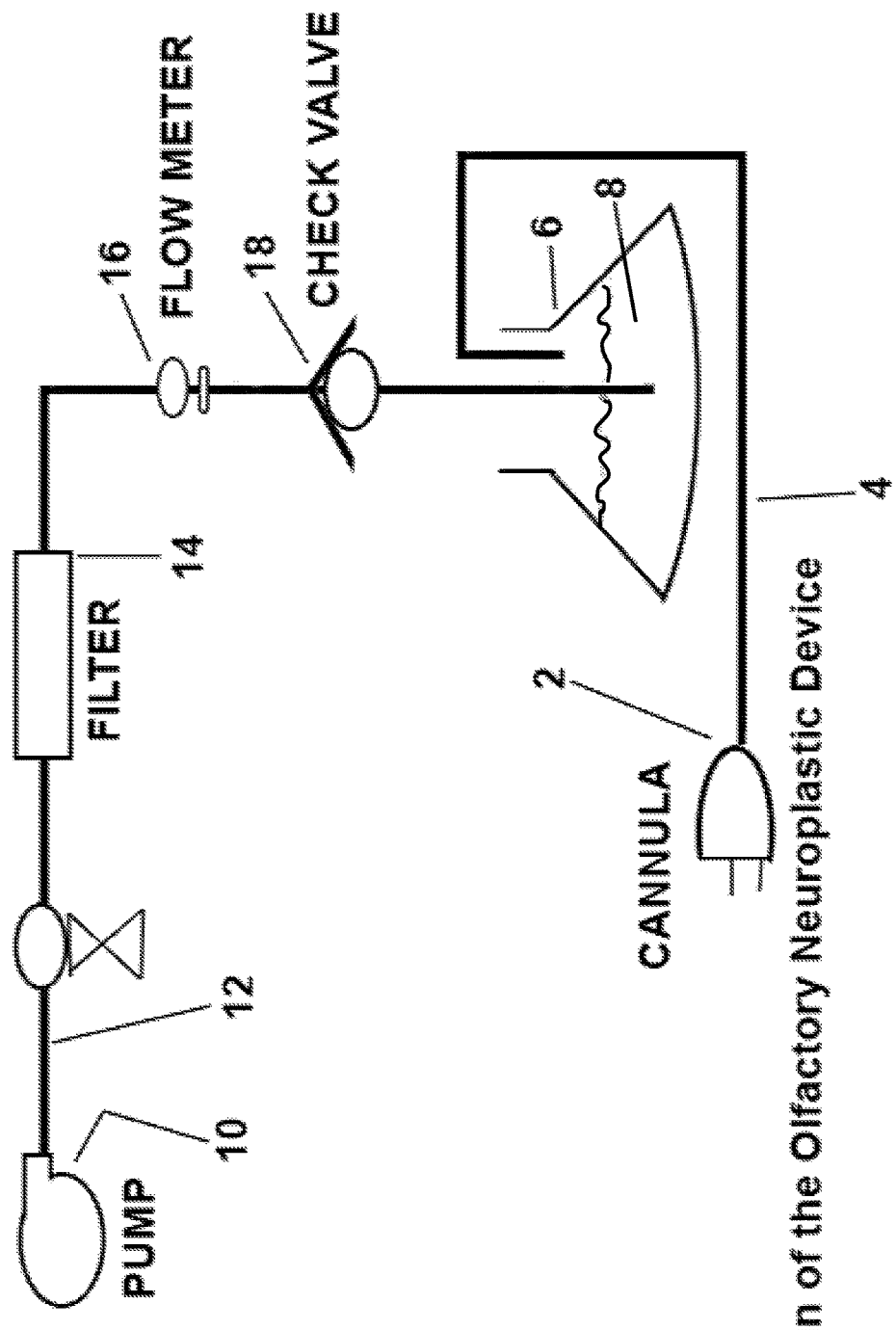
FIG. 1 is an illustration of the device used to practice the method described herein.
Figure 2:
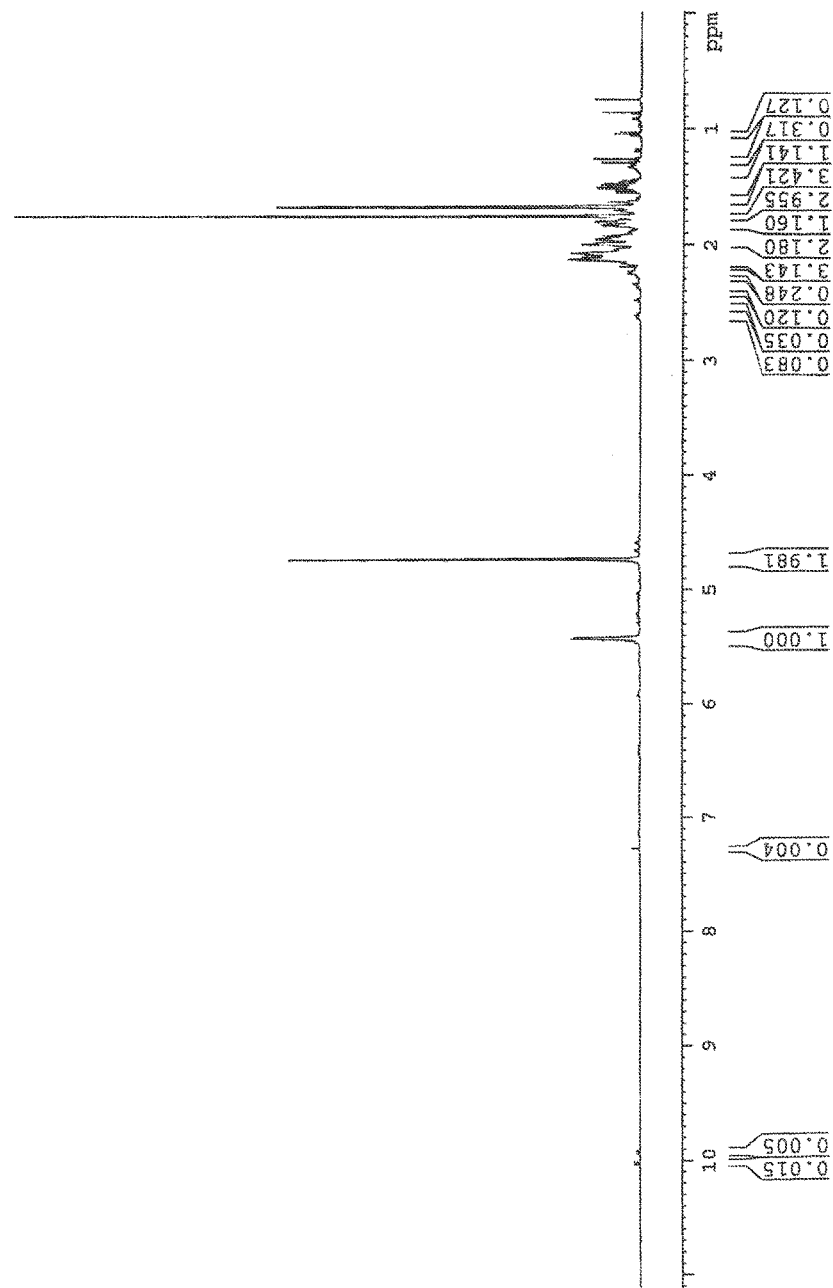
FIG. 2 illustrates a Nuclear Magnetic Resonance spectra of the odorant of lemon.
Figure 3:
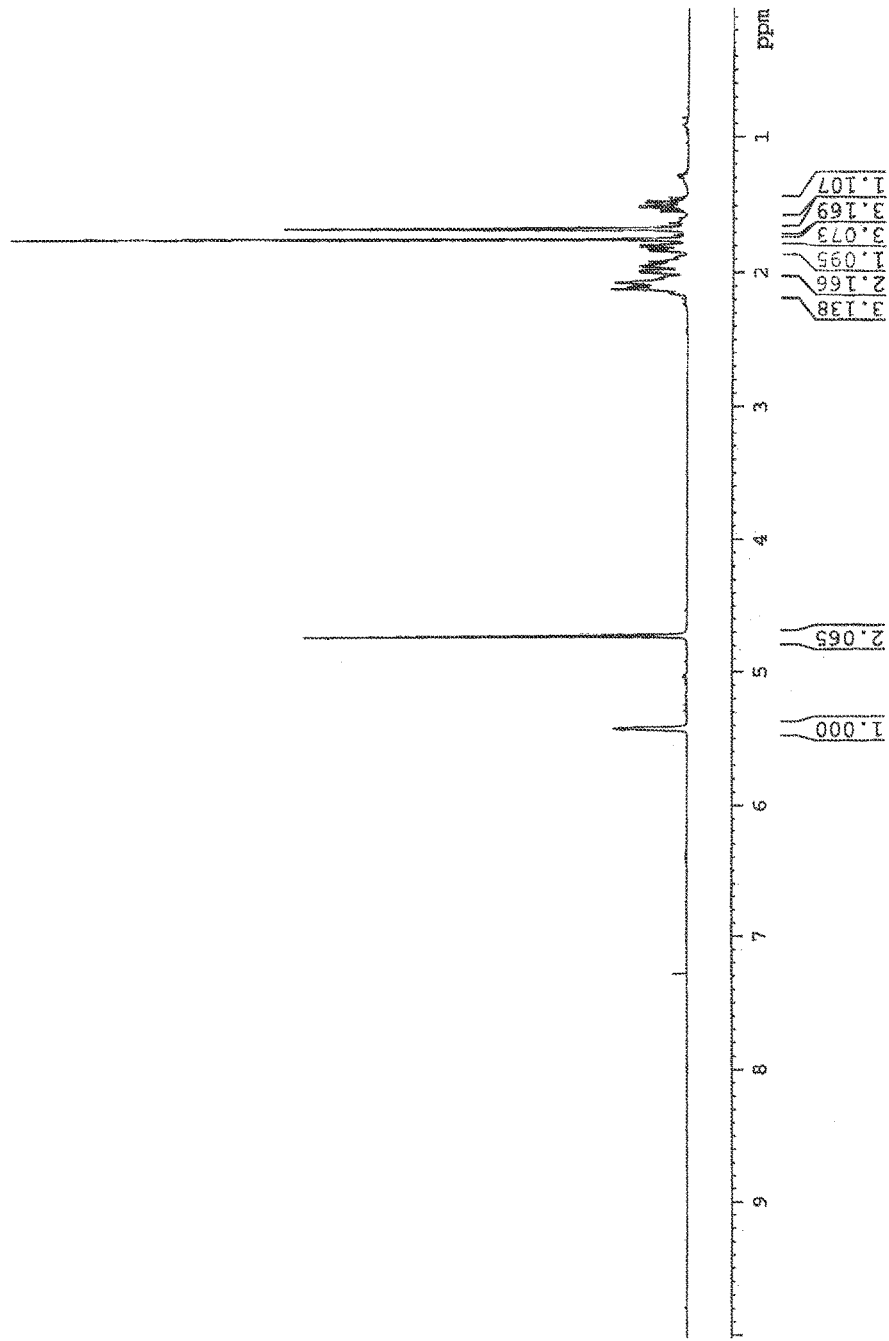
FIG. 3 illustrates a Nuclear Magnetic Resonance spectra of the odorant of sweet orange.
Figure 4:
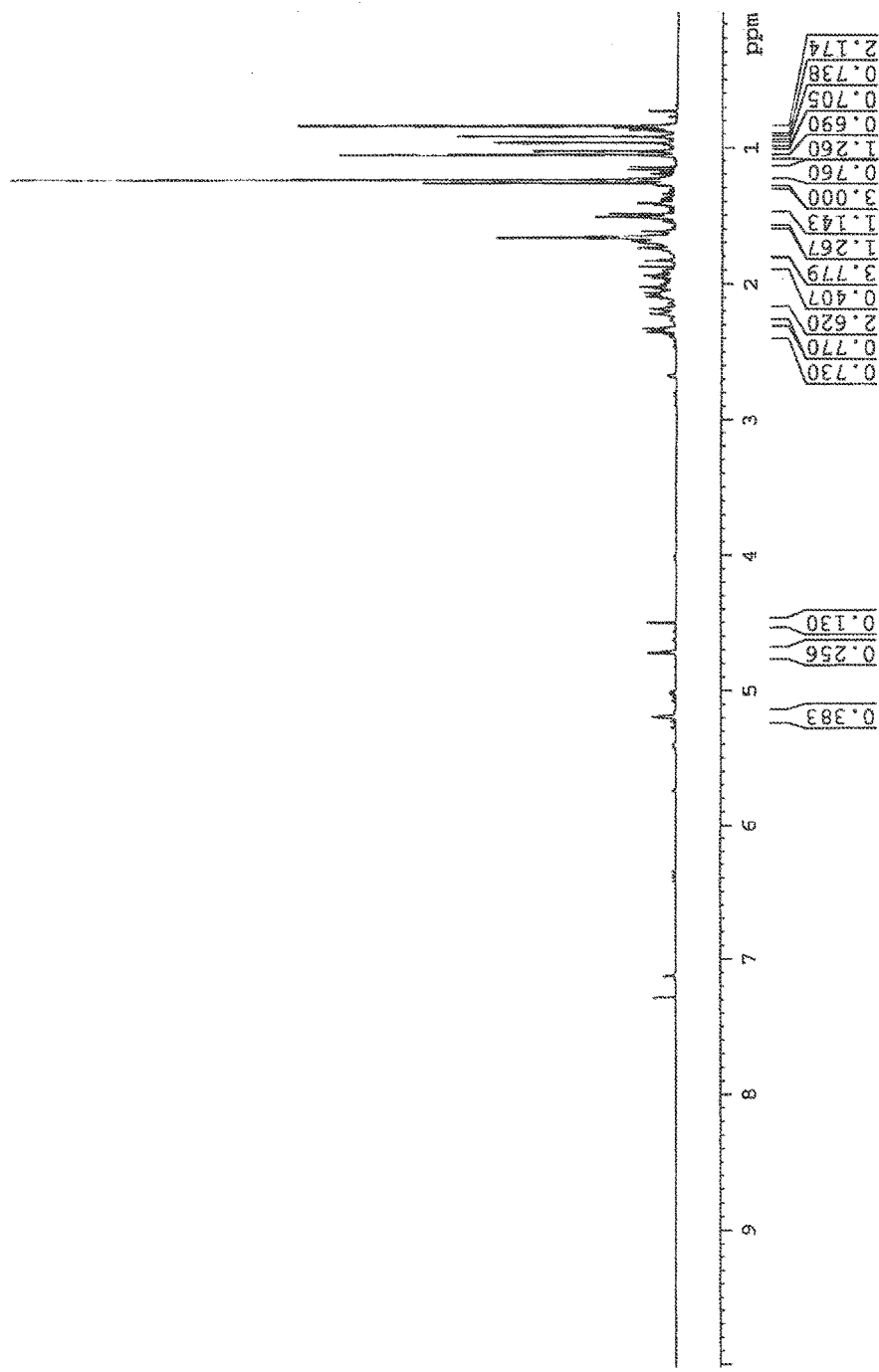
FIG. 4 illustrates a Nuclear Magnetic Resonance spectra of the odorant of rosemary.
Figure 5:
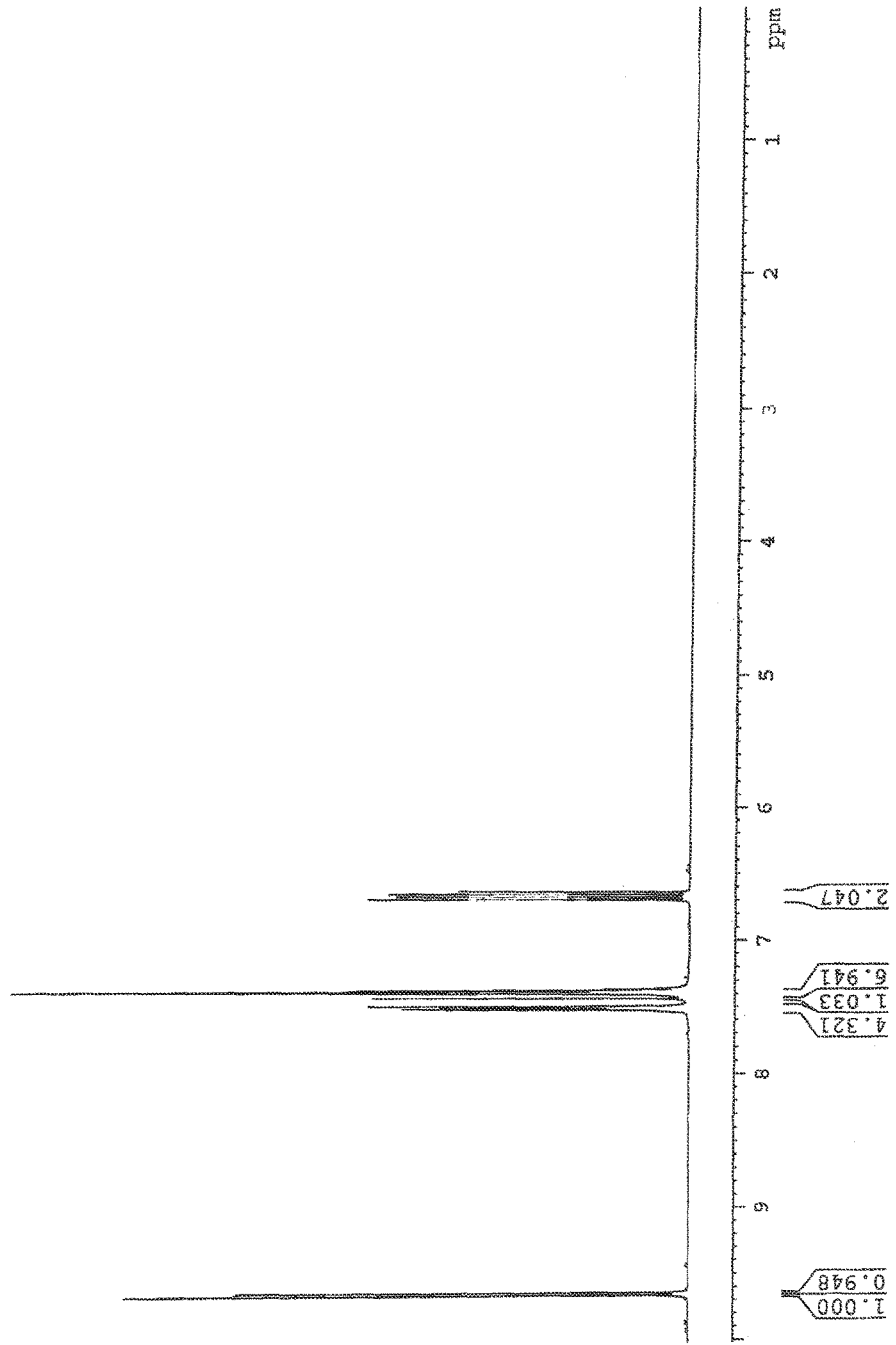
FIG. 5 illustrates a Nuclear Magnetic Resonance spectra of the odorant of cinnamon.

The apparatus includes cannula 2 having a conduit 4 into an odorant chamber 6 containing a blend of odorants 8. Pump 10 pumps air at a positive pressure through conduit 12 to filter 14 and flow meter 16 past check valve 18 into the odorant chamber 6. The air under positive pressure sweeps the odorants from the blend of odorants into conduit 4 and pushes the odorants through cannula 2 into the nose of the user.

In the important aspect, the blend of odorants includes sweet orange also called citrus sinensis. Bergamont orange also called citrus bergamia also can be used in lieu of sweet orange or blended with sweet orange. The blend further includes lemon oil also called citrus limon. As used herein, "citrus," as opposed to "citrus limon" means sweet orange or bergamont orange. The odorant blend also includes Cinnamon oil also known as *cinnamomum zeylanicum* and rosemary oil also called *rosmarinus officinalis*. Odorants which are not from a botanical source such as *cinnamomum zeylanicum*, but are flavorings which mimic the botanical sourced odorant also may be used. The individual odorants range in concentration of from about 0.5 weight percent to about 6.0 weight percent in the odorant chamber 6 and are delivered at an air/odorant rate of from about 0.5 to about 2 liters per minute. The odorant are diluted in mineral oil to obtain the latter concentration range. The device is powered by electricity through a 9V adapter plugged to any electrical source, such as a wall outlet.

In an important aspect, the apparatus is portable to permit treatment over a day/evening. In this aspect, the pump is operated with DC current being supplied by a rechargeable battery. The apparatus has a housing to accommodate the battery and an outlet to effect recharging.

Tests involving a blend of sweet orange, bergamont orange, citrus limon, cinnamon and rosemary were conducted on volunteers with each odorant dispersed in mineral oil at a concentration of 3 weight percent at an air/odorant flow rate of 0.5 liters/minute. The subjects were subjected to application of the odorant blend at the aforedescribed positive pressure for two weeks at 12 hours per day. Tests of memory functions are shown in the table below:

| CVLT Recognition/Recall | Pre-OND | Post-OND |
| --- | --- | --- |
| Total Recognition Raw Score | 12 | 16 |
| Recognition Z score | −2.5 | 0 |
| Total False Positives | 10 | 0 |
| Total False Positives Z | 3.5 | −0.5 |
| Short Delay Free Recall | 5 | 15 |
| Short Delay Free Recall Z | −3 | 1 |
| Short Delay Cued Recall | 6 | 16 |
| Short Delay Cued Recall Z | −3 | 1 |

The result support increased recognition and markedly increased free by 200% and cued by 150% short-term memory recall in this volunteer following Olfactory Treatment Delivery System (OND treatment). Moreover, it was found that the treatment increased the sense of smell. Of two volunteers, one had a remarkable anosmia and was unable to identify the n-butanol odorant at the maximum concentration supplied in the olfact-combo olfactometer. After 4 weeks of OND, be identified up to the $6^{th}$ dilution of the n-butanol (maximum is $9^{th}$ dilution). Significant changes in the scores for odor identification, odor memory and odor discrimination were also observed for both volunteers.

What is claimed is:

1. A kit for treating a human afflicted with a neurodisorder comprising:
   an apparatus which administers a blend of odorants, the apparatus comprising:
   a pump;
   a line which is used for supplying air to a vessel configured to contain the blend of odorants within the kit;
   a line from the vessel to a cannula configured for lodgment into the nose of a human, the pump configured to provide a positive pressure and a flow of gas into the cannula and nose of the human at a rate of from about 0.5 to about 2 liters per minute;
   wherein the kit comprises a therapeutically effective amount of at least two odorants selected from the group consisting of citrus, rosemary, cinnamon, banana oil, cumin, vanillin, garlic, paprika, curry, nutmeg, thyme, tarragon, celery, ginger, lavender, marjoram, basil leaves, cardamom, cloves, chocolate and anise, the odorants are dispersed into pharmaceutically acceptable oil which solvates the odorants and the odorants are each in a concentration in the range of from about 0.5 weight % to about 6.0 weight %, the pump is configured to provide a positive pressure to create a flow of oxygen and odorant blend through the nose of the human, the concentration of the blend, the ratio of odorants, and the rate of flow of the blend of odorants and oxygen.

2. The kit of claim 1, wherein the odorant blend comprises citrus, rosemary, cinnamon.

3. The kit of claim 1, wherein the pharmaceutically acceptable oil is mineral oil.

\* \* \* \* \*